United States Patent [19]

Clossick

[11] Patent Number: 4,945,920
[45] Date of Patent: Aug. 7, 1990

[54] TORQUEABLE AND FORMABLE BIOPSY FORCEPS

[75] Inventor: James P. Clossick, Miami Lakes, Fla.

[73] Assignee: Cordis Corporation, Hialeah, Fla.

[21] Appl. No.: 262,277

[22] Filed: Oct. 25, 1988

Related U.S. Application Data

[63] Continuation-in-part of Ser. No. 172,774, Mar. 28, 1988, abandoned.

[51] Int. Cl.⁵ ............................................. A61B 10/00
[52] U.S. Cl. ..................................... 128/751; 606/205
[58] Field of Search ......................... 128/749, 751–755, 128/321–325, 772, 656–658, DIG. 14, DIG. 18; 604/280–282; 606/205–209

[56] References Cited

U.S. PATENT DOCUMENTS

| | | | |
|---|---|---|---|
| 3,585,707 | 6/1971 | Stevens | 29/427 |
| 3,964,468 | 6/1976 | Schulz | 128/751 |
| 4,425,919 | 1/1984 | Alston, Jr. et al. | 128/658 |
| 4,646,751 | 3/1987 | Maslanka | 128/751 |
| 4,655,219 | 4/1987 | Petruzzi | 128/321 |
| 4,665,604 | 5/1987 | Dubowik | 604/282 X |
| 4,721,116 | 1/1988 | Schintgen et al. | 128/751 |
| 4,739,768 | 4/1988 | Engelson | 604/282 X |
| 4,763,668 | 8/1988 | Macek | 128/751 |

Primary Examiner—Angela D. Sykes
Attorney, Agent, or Firm—Henry W. Collins; Thomas R. Vigil

[57] ABSTRACT

The biopsy forceps comprises a handle portion having a distal end, an elongate tubular torqueable and formable body assembly and a forceps assembly. The tubular body assembly includes a coil spring guide wire having a proximal portion and a distal portion extending between the handle portion and the forceps assembly. A first tubing or covering over the proximal portion of the coil spring guide wire extends from the handle portion towards the forceps assembly. The first tubing has a distal end and a proximal end, and has a high resistance to twisting and a high transmission of torque applied thereto. A second tubing or covering of formable material is received over and tightly engages the distal portion of the coil spring guide wire, and imparts a high formability to the distal portion of the coil spring guidewire. The second tubing or covering has a distal end, a proximal end and extends rearwardly from the forceps assembly to a distal end of the high torque transmitting first tubing or covering. The second tubing or covering overlaps the distal end of the first tubing and defines a tip portion of the elongate torqueable and formable body assembly.

13 Claims, 2 Drawing Sheets

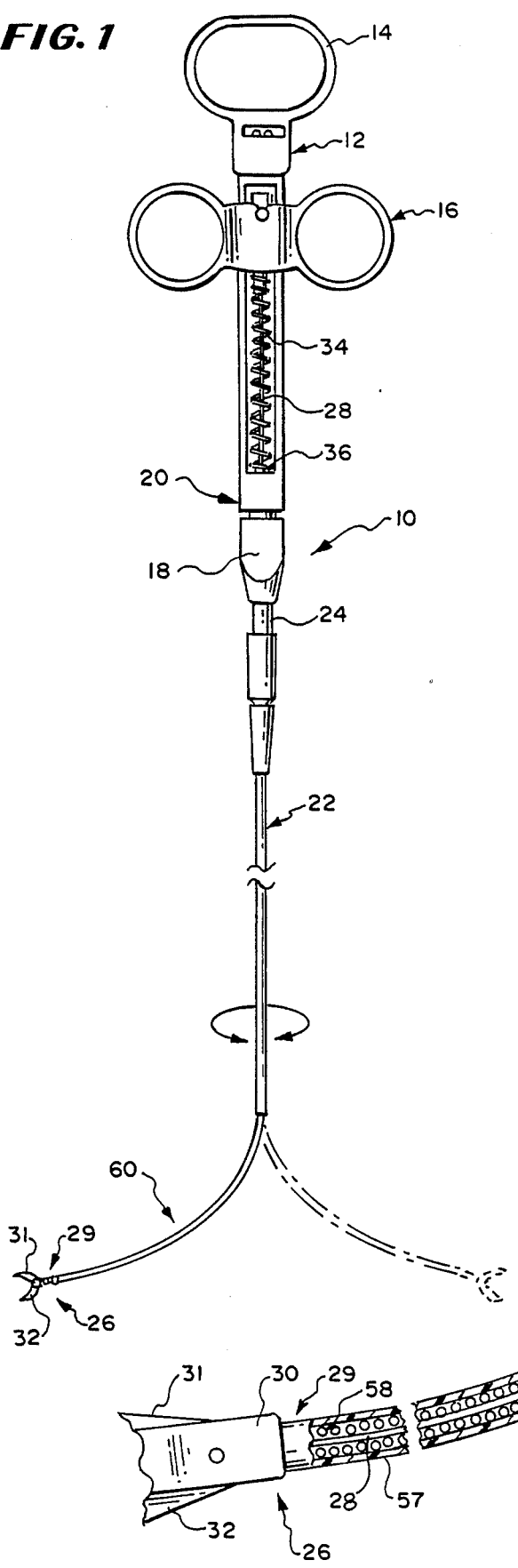
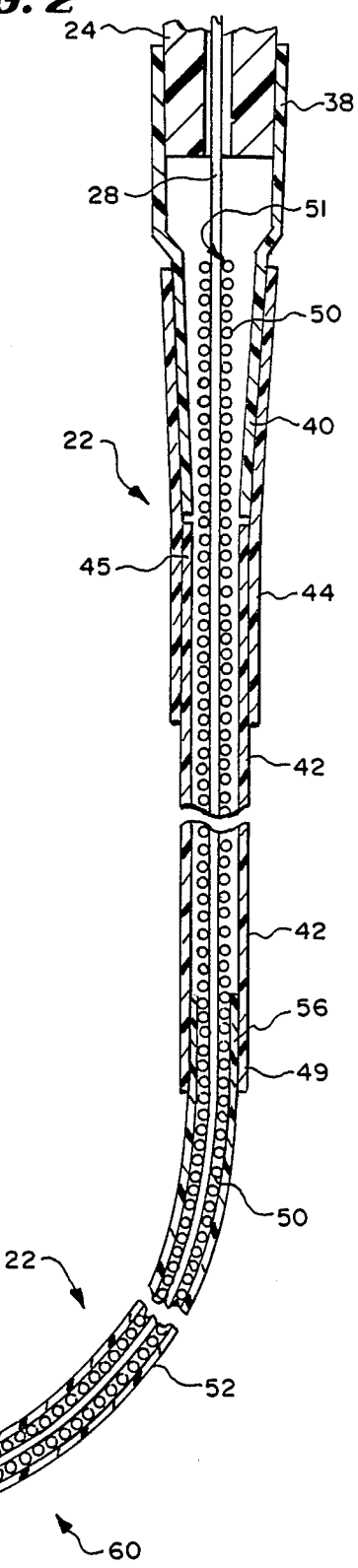
FIG. 1
FIG. 2

4,945,920

TORQUEABLE AND FORMABLE BIOPSY FORCEPS

CROSS-REFERENCE TO RELATED APPLICATIONS

This application is a Continuation-in-Part Application of U.S. Application Ser. No. 07/172,774 filed on Mar. 28, 1988 for: TORQUEABLE AND FORMABLE BIOPSY FORCEPS, now abandoned.

BACKGROUND OF THE INVENTION

1. Field of the Invention

The present invention relates to a biopsy forceps and more specifically to a biopsy forceps having an elongate tubular body assembly which includes a high torque transmitting portion and a flexible tip or end portion.

2. Description of the Prior Art

Heretofore, various biopsy forceps have been proposed and are in wide use in obtaining a biopsy tissue sample. Such biopsy forceps typically include a coil spring guide wire extending between a handle portion and a forceps assembly. The forceps assembly includes a body that is fixed to the distal end of the coil spring guide wire. A stylet or control wire is received within the lumen of the coil spring guide wire and is connectable to a trigger member movably mounted within the handle portion of the biopsy forceps to which the proximal end of the coil spring guide wire is coupled.

A pair of movable forceps are mounted to the body of the forceps assembly, and to the control wire, such that forward movement of the control wire causes the forceps to move outwardly away from each other and rearward movement of the control wire causes the forceps to come together and capture tissue therebetween.

In the use of such a biopsy forceps, rotation of the handle portion results in some twisting of the coil spring guide wire and the transmission of torque to the coil spring guide wire.

At times body fluids and blood can pass through space between adjacent coils of the coil spring guide wire, and gain access to the biopsy forceps, contaminating same.

Examples of previously proposed biopsy instruments, including biopsy forceps, are disclosed in the following U.S. Pat. Nos.:

| U.S. Pat. No. | Patentee |
| --- | --- |
| 3,964,468 | Schulz |
| 4,646,751 | Maslanka |
| 4,655,219 | Petruzzi |
| 4,721,116 | Schingten et al |

The Maslanka U.S. Pat. No. 4,646,751 discloses a biopsy forceps including an operating cable which is surrounded by a cable jacket, the cable jacket being in the form of a coiled spring. The cable jacket is surrounded by a plastic covering. In the disclosed biopsy forceps, a fluid inlet tube is provided for introducing cleaning fluid into the interior of the cable jacket.

As will be described in greater detail hereinafter, the biopsy forceps of the present invention differs from the previously proposed biopsy forceps by providing a torqueable and formable elongate body assembly which includes, according to one aspect, a coil spring guide wire with a first tubing or covering which is provided over a proximal portion of the coil spring guide wire, and which has high torque transmission characteristics, and, according to a second aspect, a second tubing or covering which is provided over a distal or tip portion of the coil spring guide wire, and which is made of a formable material and placed on the coil spring guide wire in a tight manner which gives the distal portion of the coil spring guide wire with the second tubing or covering thereon a high degree of formability.

SUMMARY OF THE INVENTION

According to the invention there is provided a biopsy forceps comprising a handle portion having a distal end, an elongate tubular body assembly and a forceps assembly, said tubular body assembly including a coil spring guide wire having a proximal portion and a distal portion extending between said handle portion and said forceps assembly, and a tubing or covering of formable material received over and tightly engaging at least said distal portion of said coil spring guide wire to form with said coil spring guide wire a plastic tubing assembly for imparting a high formability to said distal portion of said coil spring guidewire, said tubing or covering being heat shrunk on and over said distal portion of said coil spring guidewire thereby to form inwardly extending annular/spiral ribs of tubing or covering material extending into generally V shaped spaces between coils of said coil spring guidewire and said plastic tubing assembly of said coil spring guidewire and said tubing therearound being physically deformable to a desired shape and being able to hold that shape until deformed to another shape thereby defining a formable/deformable tip portion.

Also according to the invention there is provided a biopsy forceps comprising a handle portion having a distal end, an elongate tubular body assembly and a forceps assembly, said tubular body assembly including a coil spring guide wire having a proximal portion and a distal portion extending between said handle portion and said forceps assembly, and a tubing or covering over and against said proximal portion of said coil spring guide wire extending from said handle portion towards said forceps assembly, said tubing having a distal end and a proximal end and including a first inner extrusion of plastic material covered by a tubular envelope of braided material which in turn is covered by a second outer extrusion of plastic material thereby to provide a composite tubing having a high resistance to twisting and a high transmission of torque applied thereto thereby to provide the combination of said tubing on said coil spring guidewire with a very high resistance to twisting.

Further according to the invention there is provided a biopsy forceps comprising a handle portion having a distal end, an elongate tubular torqueable and formable body assembly and a forceps assembly, said tubular body assembly including a coil spring guide wire having a proximal portion and a distal portion extending between said handle portion and said forceps assembly, a first tubing or covering over said proximal portion of said coil spring guide wire extending from said handle portion towards said forceps assembly, said first tubing or covering having a distal end and a proximal end, and having a high resistance to twisting and a high transmission of torque applied thereto, and a second tubing or covering of formable material received over and tightly engaging said distal portion of said coil spring guide wire to form with said coil spring guidewire a plastic tubing assembly for imparting a high formability to said distal portion of said coil spring guidewire, said second tubing or covering having a distal end, a proximal end and extending rearwardly from said forceps assembly to a distal end of said high torque transmitting first tubing or covering, said distal end of said first tubing or covering being in overlapping relationship with said proximal end of said second tubing, said second tubing or covering being heat shrunk on and over said distal portion of said coil spring guidewire thereby to form said second tubing or covering with inwardly extending annular ribs of material which extend into spaces between coils of said coil spring guidewire, said plastic tubing assembly including said coil spring guidewire and said second tubing or covering defining a tip portion of said elongate torqueable and formable body assembly which is physically deformable to a desired shape and which will hold that shape until deformed to another shape.

Still further according to the invention there is provided a method for imparting torqueability and formability to a biopsy forceps of the type comprising a handle portion having a distal end, an elongate tubular body assembly and a forceps assembly with said tubular body assembly including a coil spring guide wire having a proximal portion and a distal portion extending between said handle portion and said forceps assembly, said method comprising the steps of: placing a first tubing or covering over said proximal portion of said coil spring guide wire extending from said handle portion towards said forceps assembly, said first tubing or covering having a distal end and a proximal end; providing said first tubing or covering with a high resistance to twisting and a high transmission of torque applied thereto; placing a second tubing or covering of formable material over said coil spring guidewire; heat shrinking said second tubing or covering around and into said coil spring guidewire to tightly engage said distal portion of said coil spring guidewire in a manner whereby inwardly extending annular ribs of said second tubing or covering are formed which extend into the spaces between adjacent coils of said coil spring guidewire to impart a high formability to said distal portion of said coil spring guidewire, whereby said combination of said heat shrunk second tubing or covering and said coil spring guidewire are physically deformable to a desired shape and will hold that shape until deformed to another shape.

BRIEF DESCRIPTION OF THE DRAWING

FIG. 1 is a plan view of a torqueable and formable biopsy forceps made according to the teachings of the present invention.

FIG. 2 is a longitudinal sectional view of an elongate torqueable and formable body assembly of the torqueable and formable biopsy forceps of the present invention with portions broken away.

DESCRIPTION OF THE PREFERRED EMBODIMENT

Figure 3:
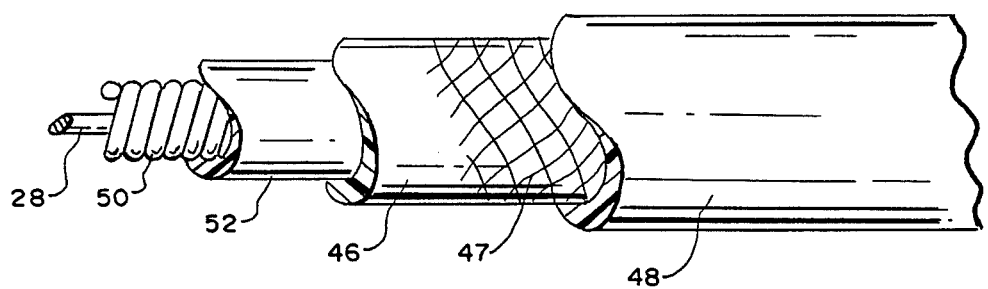
FIG. 3 is an enlarged fragmentary plan view of a proximal portion of the torqueable formable body assembly with portions broken away to show the components of a torqueable tubing which components include an inner tubing, a layer of tubular wire mesh and an outer tubing.

Referring now to the drawings in greater detail, there is illustrated in FIG. 1 a plan view of a biopsy forceps 10 which includes a handle portion 12 having a thumb receiving end ring 14, a generally FIG. 8 shaped trigger 16 movably mounted to the handle portion 14, a hub 18 mounted at a distal end 20 of the handle portion 12 and a torqueable and formable flexible elongate body assembly 22 which extends from a distal end 24 of the hub 18 to a forceps assembly 26.

The torqueable and formable body assembly 22 is constructed in accordance with the teachings of the present invention, as will be described in greater detail hereinafter.

As shown in FIG. 1 a stylet or operating control wire 28 extends from the movable trigger 16 within the handle portion 12 and the torqueable formable body assembly 22 to the forceps assembly 26 and is connected thereto.

The forceps assembly 26 is of conventional construction and includes a body portion 30 which is fixed to a distal end 29 of the elongate body assembly 22 and a pair of forceps 31 and 32 pivotally connected to the body portion 30 and movable between an open position shown in FIG. 1 to a closed position upon movement of the control wire 28 actuated by the trigger 16. Typically, a spring 34 is provided in the handle portion 12, as shown in FIG. 1, between a wall 36 therein and the movable trigger 16 so as to bias the trigger 16 rearwardly to a forceps closed position.

In use, after the biopsy forceps has been inserted through a blood vessel into a heart chamber, an operator would move the trigger 16 forwardly to move the forceps 31, 32 of the forceps assembly 26 to an open position, as shown, for capturing a tissue specimen. Then, release of pressure on the trigger 16 allows the trigger 16 to move to the position shown in FIG. 1 where the forceps 31, 32 of the forceps assembly 26 are closed to facilitate withdrawal of the forceps 31, 32 with the captured specimen therein.

As shown in FIG. 2, the torqueable and formable body assembly 22 includes a first sleeve 38 which is received over the distal end 24 of the hub 18 and which has a tapering or conical distal end portion 40 which tapers to the diameter of a torqueable tubing 42 to be described in greater detail hereinafter. Then the torqueable formable elongate body assembly 22 includes a second, tightly fitting sleeve 44 which is received tightly over or shrunk around the conical distal end portion 40 of the first sleeve 38 and a proximal end 45 of the torqueable tubing 42.

Although not shown in FIG. 2, it will be understood that the torqueable tubing 42 extends for a suitable length longer than that shown.

This torqueable tubing 42 is preferably a three layer tubing as shown including a first inner plastic extrusion 46, a tubular envelope of braided material 47 such as a stainless steel braid mesh, and a second outer plastic extrusion 48 of the type disclosed in U.S. Pat. No. 3,585,707 or in U.S. Pat. No. 4,425,919, the disclosures of which are incorporated herein by reference. Such a tubing 42 is flexible to allow the tubing 42 to move laterally or bend when it is inserted into a blood vessel and moved along the changing curved pathway of the blood vessel and yet is highly resistive to twisting in view of its construction so that a torque applied to the proximal end 46 of the tubing 42 is transmitted to a distal end 49 of the tubing 42 with very little twisting of the tubing 42. The high resistance to twisting is greatly enhanced by the combination of the guidewire 50 and the tubing 42 as a result of the guidewire presenting a stiff cylindrical shell about and against which the tubing 42 is received thereby preventing any distortion or kinking of the tubing 42 which could occur if the guidewire 50 were not present, e.g., as one would kink a garden hose by twisting it.

Within the torqueable tubing 42 there is received a coil spring guidewire 50 (FIGS. 2 and 3) of conventional construction which defines an inner lumen 51 that receives the stylet or control wire 28 which extends between the trigger 16 and the forceps assembly 26. Such coil spring guidewire 50 provides firmness to the torqueable formable body assembly 22 while permitting flexing of the torqueable formable body assembly 22. The torqueable tubing 42 can be formed as a separate tubing on a mandrel and then placed over the coil spring guidewire 50 or coated directly onto the coil spring guidewire 50.

Between the forceps assembly 26 and the distal end 48 of the non-twisting torqueable tubing 42 is a second tubing 52 which is made of a smooth flexible and formable plastic material such as polyolefin or Teflon TM (tetrafluorethylene). The second tubing 52 is created by first coating or covering the coil spring guidewire 50 with the polyolefin or Teflon TM material or other plastic material which is extruded onto the guidewire 50 or coated thereon by dipping the guidewire 50 into liquid plastic material.

Figure 4:
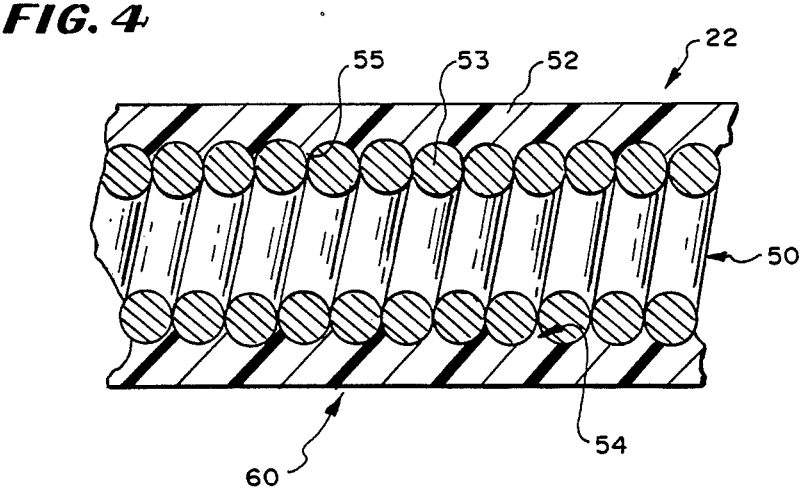
FIG. 4 is a fragmentary elongate sectional view of a distal portion of the torqueable and formable body assembly and shows an outer or second tubing of formable material which is heat shrunk about a coil spring guide wire of the torqueable and formable body assembly.

The second tubing 52 is shown in larger detail in FIG. 4 and is heat shrunk about the coil spring guidewire 50 to closely surround coils 53 of the coil spring guidewire 50 and spaces 54 between coils 53 of the coil spring guidewire 50 to render the coil spring guidewire 50 with such Teflon TM coating or tubing 52 heat shrunk thereon (with or without the coil wire 28 therein) more formable than in previous biopsy forceps.

Typically, in forming the plastic coating, covering or tubing 52 on the coil spring guidewire 50, a heat source is applied to the outer surface of the coating or tubing 52 that has been initially placed over the coil spring guidewire 50. The heat causes the tubing 52 to shrink over the outer surface of the coil spring guidewire 50 as shown in FIG. 4.

Figure 5:
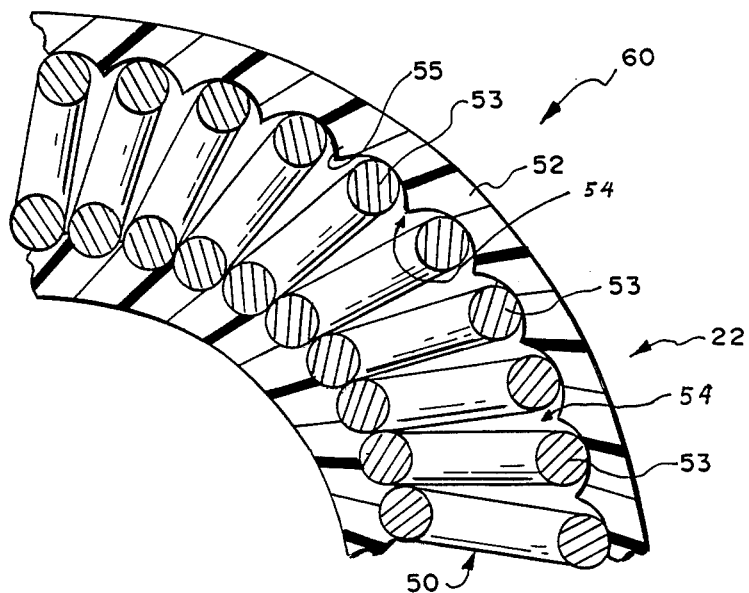
FIG. 5 is a fragmentary elongate sectional view of the distal portion of the torqueable and formable body assembly shown in FIG. 4 but bent to form a bend in the distal portion.

As the tubing 52 shrinks, it encloses the coils 53 and additionally tends to fill in the general V-shaped spaces, notches or gaps 54 between the coils 53 with annular (spiral) ribs 55. The filling of the gaps 54 between the coils 53, as shown in FIGS. 4 and 5, allows the coiled spring guidewire to hold a formed shape as shown in FIG. 5. In this respect, the tight fit of the heat shrunk tubing 52 limits the movement of the coils 53 radially outwardly, and the ribs 54 thereof limit movement of the coils 53 axially relative to adjacent coils 53, thereby to prevent major displacement of any one of the coils 53 and kinking of the guidewire 50.

This construction of the second plastic tubing, coating or covering 52 not only makes the assembly more formable to permit it to be shaped for placement in an irregularly shaped blood vessel passageway and take the shape thereof but also provides an easily sliding tubing 52, particularly where Teflon TM is used, which has a low coefficient of friction to facilitate sliding movement of the second tubing, coating or covering 52 through an irregularly shaped blood vessel or other body passageway.

A proximal end 56 of the second tubing or covering is received within the distal end 48 of the first tubing 42 and a distal end 57 of the second tubing extends over a distal end 58 of the coil spring guidewire 50. The body portion 30 of the forceps assembly 26 which is fixed to the distal end 58 of the coil spring guidewire 50.

In FIG. 5, it is apparent that the ribs 55 hold the coils 53 against axial movement even when the tip portion 60 is bent.

In this way, the tip portion 60 of the tubular body assembly 22 of the biopsy forceps 10 defined by the portion of the coil spring guidewire 50 having the second tubing, coating or covering 52 thereon can be manually formed by a doctor to meet his specific needs. The highly formable tip portion including the tubing or coating 52 tightly engaging the outer surface of the coil spring guidewire 50, enables the doctor to manually form the tip portion 60 without kinking the coil spring guidewire 50. The tip portion 60 then can be formed and reformed to the patient's specific needs.

The forming of the tip portion 60 preferably is achieved by pulling the coil spring guidewire 50 with the heat shrunk tubing or covering 52 thereon through the fingers while slightly bending the tip portion 60. This procedure is repeated until the desired curvature is achieved.

The first tubing 42 in conjunction with the second tubing 52 provides good torque transmission through the torqueable formable elongate body assembly 22 to enable specific and accurate location of the forceps assembly 26 adjacent a heart wall. This greater torqueability aids in the crossing of heart valves while the second tubing 52 and the portion of the coil spring guidewire 50 therein can be formed to the patient's specific needs.

Additionally, by providing the first and second coatings or tubings 42 and 52 over the coil spring guidewire 50, back purging of blood and body fluids through interstices between coils of the coil spring guidewire 50 and through the lumen 51 thereof and back to other parts of the biopsy forceps 10 such as the handle portion 12 thereof, is inhibited if not altogether prevented.

Preferably, the outer plastic extrusion of the first tubing 42 is made of Ducor TM and the second tubing or coating 52 is made of Teflon TM.

From the foregoing description, it will be apparent that the torqueable and formable biopsy forceps of the present invention has a number of advantages, some of which have been described above, and others of which are inherent in the invention.

Also, it will be apparent that modifications can be made to the torqueable and formable biopsy forceps 10 without departing from the teachings of the invention. Accordingly, the scope of the invention is only to be limited as necessitated by the accompanying claims.

I claim:

1. A biopsy forceps comprising a handle portion having a distal end, an elongate tubular torqueable and formable body assembly and a forceps assembly, said tubular body assembly including a coil spring guide wire having a proximal portion and a distal portion extending between said handle portion and said forceps assembly, a first tubing or covering over said proximal portion of said coil spring guide wire extending from said handle portion towards said forceps assembly, said first tubing or covering having a distal end and a proximal end, and having a high resistance to twisting and a high transmission of torque applied thereto, and a second tubing or covering or formable material received over and tightly engaging said distal portion of said coil spring guide wire to form with said coil spring guide wire a plastic tubing assembly for imparting a high formability to said distal portion of said coil spring guide wire, said second tubing or covering having a distal end, a proximal end and extending rearwardly from said forceps assembly to a distal end of said high torque transmitting first tubing or covering, said end of said first tubing or covering being in overlapping relationship with said proximal end of said second tubing, said second tubing or covering being heat shrunk on and over said distal portion of said coil spring guide wire thereby to form said second tubing or covering with inwardly extending annular ribs of material which extend into spaces between coils of said coil spring guide wire and said plastic tubing assembly including said coil spring guide wire and said second tubing or covering defining a tip portion of said elongate torqueable and formable body assembly which is physically deformable to a desired shape and which will hold that shape until deformed to another shape.

2. The biopsy forceps of claim 1, wherein said second formable tubing or covering is made of a material which has a low coefficient of friction.

3. The biopsy forceps of claim 1 wherein said second tubing or covering is made of tetrafluorethylene.

4. The biopsy forceps of claim 1 wherein said distal end of said first tubing extends over the proximal end of said second tubing.

5. The biopsy forceps of claim 1 wherein said first tubing includes an extrusion of a torque-transmitting material sold under the trademark DUCOR.

6. The biopsy forceps of claim 1 wherein said first tubing includes a first inner extrusion of a plastic material, covered by a tubular envelope of braided material, which in turn is covered by a second, outer extrusion of plastic material.

7. The biopsy forceps of claim 6 wherein said braided material is a small gauge stainless steel material.

8. The biopsy forceps of claim 1 wherein said tubular body assembly includes a first sleeve which has a proximal end received over a distal end of the handle portion of the biopsy forceps, a distal end and a conical distal sleeve portion which extends to the proximal end of said first tubing and a second sleeve tightly fitting around the adjacent distal end of the conical distal sleeve portion of said first sleeve and the proximal end of said first tubing.

9. A method for imparting torqueability and formability to a biopsy forceps of the type comprising a handle portion having a distal end, an elongate tubular body assembly and a forceps assembly with said tubular body assembly including a coil spring guide wire having a proximal portion and a distal portion extending between said handle portion and said forceps assembly, said method comprising the steps of: placing a first tubing or covering over said proximal portion of said coil spring guide wire extending from said handle portion towards said forceps assembly, said first tubing or covering having a distal end and a proximal end; providing said first tubing or covering with a high resistance to twisting and a high transmission of torque applied thereto; placing a second tubing or covering of formable material over said coil spring guidewire; heat shrinking said second tubing or covering around and into said coil spring guidewire to tightly engage said distal portion of said coil spring guidewire in a manner whereby inwardly extending annular ribs of said second tubing or covering are formed which extend into the spaces between adjacent coils of said coil spring guidewire to impart a high formability to said distal portion of said coil spring guidewire, whereby said combination of said heat shrunk second tubing or covering and said coil spring guide wire are physically deformable to a desired shape and will hold that shape until deformed to another shape.

10. A biopsy forceps comprising a handle portion having a distal end, an elongate tubular body assembly and a forceps assembly, said tubular body assembly including a coil spring guide wire having a proximal portion and a distal portion extending between said handle portion and said forceps assembly, and a tubing or covering over and against said proximal portion of said coil spring guide wire extending from said handle portion towards said forceps assembly, said tubing having a distal end and a proximal end and adjacent said proximal end including a first inner extrusion of plastic material covered by an intermediate tubular envelope of braided material which in turn is covered by a second outer extrusion of plastic material thereby to provide a composite tubing having a high resistance to twisting and a high transmission of torque applied thereto thereby to provide the combination of said tubing on said coil spring guidewire with a very high resistance to twisting.

11. The biopsy forceps of claim 10 wherein said tubing includes an extrusion of a torque-transmitting material sold under the trademark DUCOR.

12. The biopsy forceps of claim 10 wherein said braided material is a small gauge stainless steel material.

13. A biopsy forceps comprising a handle portion having a distal end, an elongate tubular body assembly and a forceps assembly, said tubular body assembly including a coil spring guide wire having a proximal portion and a distal portion extending between said handle portion and said forceps assembly, and a tubing or covering of formable material received over and tightly engaging at least said distal portion of said coil spring guide wire to form with said coil spring guide wire a plastic tubing assembly for imparting a high formability to said distal portion of said coil spring guide wire, said tubing or covering being heat shrunk on and over said distal portion of said coil spring guide wire thereby to form inwardly extending annular/spiral ribs of tubing or covering material extending into generally V shaped spaces between coils of said coil spring guide wire and said plastic tubing assembly of said coil spring guide wire and said tubing therearound being physically deformable to a desired shape and being able to hold that shape until deformed to another shape thereby defining a formable/deformable tip portion.

* * * * *

UNITED STATES PATENT AND TRADEMARK OFFICE
CERTIFICATE OF CORRECTION

PATENT NO. : 4,945,920
DATED : August 7, 1990
INVENTOR(S) : James P. Clossick, Miami Lakes, FL It is certified that error appears in the above-identified patent and that said Letters Patent is hereby corrected as shown below:

Column 6, line 7 "48" should be --49--

Column 7, line 6 ".or" (secon occurrence) should be --of--

Column 7, line 14 "said end" should be --said distal end--

Signed and Sealed this

Second Day of February, 1993

Attest:

STEPHEN G. KUNIN

*Attesting Officer*   Acting Commissioner of Patents and Trademarks